United States Patent

Itoh

[11] Patent Number: 5,789,639
[45] Date of Patent: Aug. 4, 1998

[54] PROCESS FOR MANUFACTURING ALKENYL COMPOUNDS

[75] Inventor: Takashi Itoh, Satte, Japan

[73] Assignees: Cosmo Oil Co., Ltd.; Petroleum Energy Center, both of Tokyo, Japan

[21] Appl. No.: 502,648

[22] Filed: Jul. 14, 1995

[30] Foreign Application Priority Data

Jul. 20, 1994 [JP] Japan .................................. 6-190080
Dec. 22, 1994 [JP] Japan .................................. 6-336045

[51] Int. Cl.$^6$ .............................. C07C 2/64; C07C 5/09; C07C 15/46; C07C 7/00
[52] U.S. Cl. .................. 585/452; 585/435; 585/446; 585/438; 585/467; 585/802
[58] Field of Search .................... 585/435, 446, 585/452, 467, 438, 802

[56] References Cited

U.S. PATENT DOCUMENTS

| | | | |
|---|---|---|---|
| 3,953,535 | 4/1976 | Shima et al. ......................... | 585/452 |
| 3,954,895 | 5/1976 | Shima et al. ......................... | 585/452 |
| 3,954,896 | 5/1976 | Shima et al. ......................... | 585/438 |
| 4,018,840 | 4/1977 | Iwata et al. .......................... | 585/432 |
| 5,329,058 | 7/1994 | Shimada et al. ..................... | 585/438 |
| 5,523,504 | 6/1996 | Itoh ..................................... | 585/438 |
| 5,527,977 | 6/1996 | Takagawa et al. ................... | 585/802 |

*Primary Examiner*—Glenn Caldarola
*Assistant Examiner*—Patricia L. Hailey
*Attorney, Agent, or Firm*—Oblon, Spivak, McClelland, Maier & Neustadt, P.C.

[57] ABSTRACT

A process for manufacturing an alkenyl compound which comprises reacting an alkylbenzene and 1,3-butadiene in the presence of metallic sodium or a combination of metallic sodium and an oxide, a hydroxide, or a salt of potassium, rubidium or an alkaline earth metal, or a mixture of these under a pressure of 1 kPa (gauge) to 30 MPa (gauge). The process can produce alkenyl compound which is an industrially valuable compound as a raw material for the manufacture of naphthalenedicarboxylic acid, a highly useful raw material of polymers, at a high yield using a small amount of metallic sodium.

7 Claims, 1 Drawing Sheet

5,789,639

PROCESS FOR MANUFACTURING ALKENYL COMPOUNDS

BACKGROUND OF THE INVENTION

1. Field of the Invention

The present invention relates to a process for manufacturing an alkenyl compound which is an industrially valuable compound as a raw material for the manufacture of naphthalenedicarboxylic acid, a highly useful raw material of polymers such as polyethylene naphthalate (PEN).

2. Description of the Background Art

In the process for manufacturing alkenyl compounds, an alkylbenzene and 1,3-butadiene are reacted in the presence of an alkali metal as a catalyst. Conventionally known catalysts used in this reaction are metallic potassium (Japanese Patent Publication (kokoku) No. 17973/1975) and a combination of metallic potassium and metallic sodium (Japanese Patent Publication (kokoku) Nos. 34570/1981, 26489/1982, and 17973/1975).

Conventional methods using these catalysts, however, have the following drawbacks.

(1) High production cost due to the use of expensive metallic potassium.

(2) Risks associated with the use of metallic potassium. Metallic potassium is highly reactive with water, moist air, and the like, and is thus ignited by merely bringing it to come into contact with them. Thus, it may ignite combustible materials, such as raw materials and reaction products.

These methods are therefore very dangerous because of the use of metallic potassium which has these characteristics.

In an effort of avoiding the use of metallic potassium, a method of using metallic sodium and an inorganic salt of potassium has been proposed (Japanese Patent Laid-open (kokai) Nos. 31935/1972, 226927/1992, and WO 91-16284).

This method does not necessarily provide industrial advantage because of (3) the requirement for special agitators, such as an emulsification apparatus, and the requirement for the use of high purity inorganic salt of potassium.

Japanese Patent Application Laid-open (kokai) No. 107569/1994 discloses a method which does not require the use of the special agitators. This patent application claims that even though the reaction is caused to proceed very little when metallic sodium and an inorganic salt of potassium are used as a catalyst while stirring the mixture using a stirrer equipped with half-moon-shaped blades, the reaction yield is greatly improved if glass balls or α-alumina balls which scrape away the surface of powdery catalysts are used together.

This method, however, has a problem that (4) rotation of the stirring blades is disturbed, causing the equipment to be unduly abraded, due to the use of glass balls or α-alumina balls with a large average diameter (about 2.0–3.0 mm).

In addition, a method of using only metallic sodium is known (Dimitrror Ch. et al. Dokl. Bolg Akad. Nuak., 33, 353 (1980)).

This method (5) requires a large amount of metallic sodium, e.g. 7.9% by weight of o-xylene, and yet gives only an extremely low yield, e.g. 31.6%.

An object of the present invention is therefore to provide a process for manufacturing an alkenyl compound from an alkylbenzene and 1,3-butadiene, which is free from all the problems (1)–(5) above.

As a result of extensive studies for achieving this object, the present inventor has found that a reaction of alkylbenzene and 1,3-butadiene under a certain prescribed pressure in the presence of a catalyst system consisting of metallic sodium alone or a combination of metallic sodium and an oxide, a hydroxide, or a salt of potassium, rubidium or an alkaline earth metal, or a mixture of these, produced the alkenyl aromatic compound at a high yield without using a large amount of metallic sodium.

SUMMARY OF THE INVENTION

Accordingly an object of the present invention is to provide a process for manufacturing an alkenyl compound which comprises reacting an alkylbenzene and 1,3-butadiene in the presence of metallic sodium under a pressure of 1 kPa (gauge) to 30 MPa (gauge).

Another object of the present invention is to provide a process for manufacturing an alkenyl compound which comprises reacting an alkylbenzene and 1,3-butadiene in the presence of metallic sodium and an oxide, a hydroxide, or a salt of potassium, rubidium or an alkaline earth metal, or a mixture of these, under a pressure of 1 kPa (gauge) to 30 MPa (gauge), said reaction is carried out in the presence of, in addition to the metallic sodium.

Other and further objects, features and advantages of the present invention will appear more fully from the following description.

DETAILED DESCRIPTION OF THE INVENTION AND PREFERRED EMBODIMENTS

Figure 1:
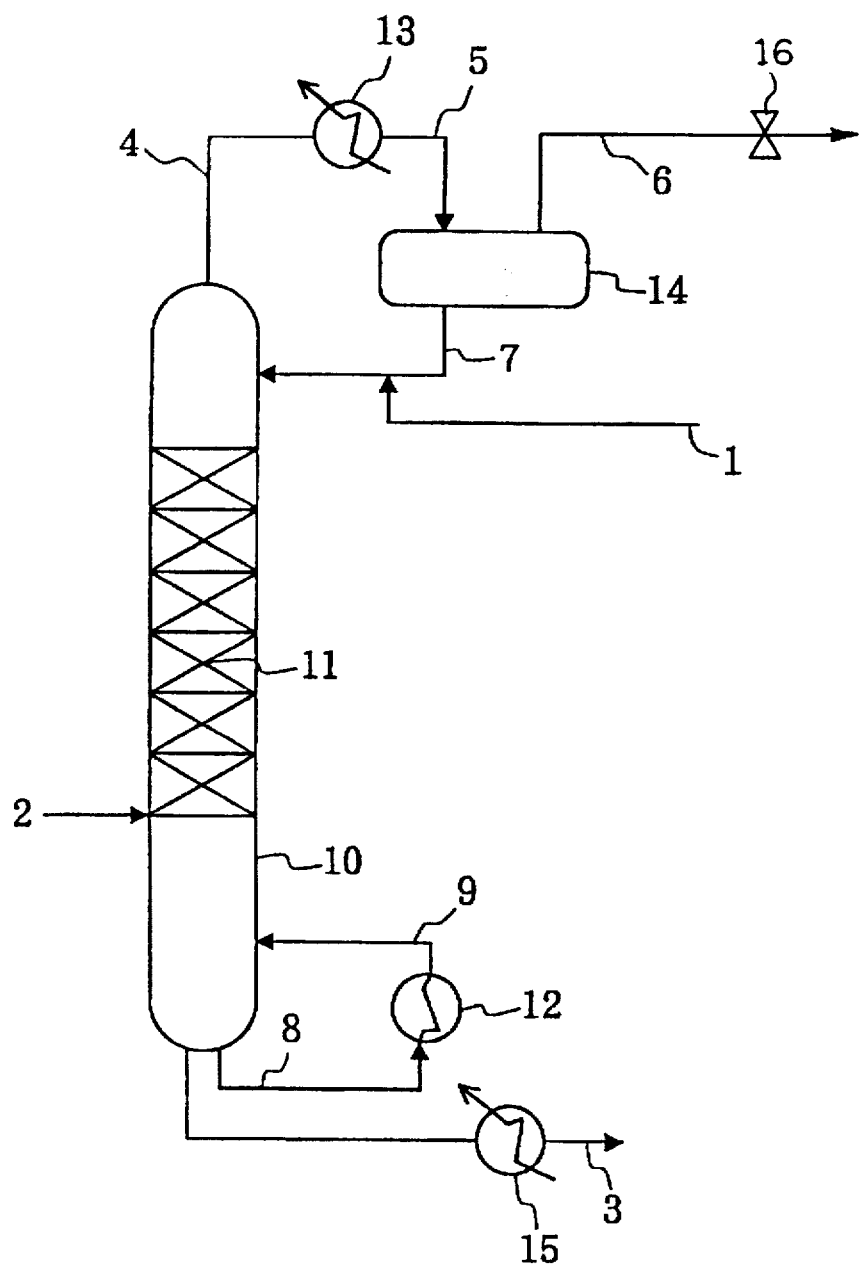
FIG. 1 is a drawing illustrating one embodiment of the device for carrying out the process of the present invention.

The alkylbenzene in the present invention denotes a compound having 1–5 groups selected from alkyl groups such as methyl group and ethyl group on benzene ring. Toluene, ethylbenzene, o-xylene, m-xylene, p-xylene, trimethylbenzene, tetramethylbenzene, and pentamethylbenzene, are given as specific examples.

It is desirable that one of these alkylbenzenes be used alone. If two or more of them are used together, it is difficult to separate each target compound at a high purity from alkenyl compounds produced by the reaction.

Further, it is desirable for the purpose of effective isolation of target compound to use an alkylbenzene with a purity as high as possible. A specific desirable purity is 95% or higher, and especially 98% or higher.

Notwithstanding this stringent purity requirement for alkylbenzene, inclusion of a slight amount of hydrocarbons having no alkyl groups, such as benzene and cyclohexane, is acceptable.

Alkylbenzene with a water content as low as possible is preferred, because the water impairs the catalyst by reducing the activity of metallic sodium. A preferred water content is below the detectable sensitivity by Karl Fischer's method which is a common measuring method of a water content, and specifically it is below several ppm.

The use of dehydrated alkylbenzene is therefore preferred.

The method for dehydrating alkylbenzenes which can be employed include a method of absorbing and separating water using an appropriate drying agent, such as activated alumina, silica gel, molecular sieve, or activated carbon; a low temperature separation method; and a method of contacting alkylbenzenes with metallic sodium or metallic potassium. Among these, the last-mentioned method, i.e. the method of contacting alkylbenzenes with metallic sodium or metallic potassium, is preferred.

There are no limitations as to the method for manufacturing 1,3-butadiene to be reacted with alkylbenzene. There are also no need for the purity of the 1,3-butadiene to be as high as the above-mentioned purity of alkylbenzene. The reaction proceeds smoothly and there are no needs for isolation of the target compound irrespective of the purity of 1,3-butadiene. Crude butadiene obtained, for example, by the dehydrogenation of butane or butene can be used as is, or 1,3-butadiene obtained by purification of this crude butadiene by extraction or the like can be also used.

Nevertheless, a lower water content of 1,3-butadiene is more desirable from the same reasons as mentioned above in connection with alkylbenzenes. Specifically, a preferred water content of 1,3-butadiene is several ppm. Thus, the use of dehydrated 1,3-butadiene is preferred.

The method for dehydrating 1,3-butadiene which can be employed include a method of absorbing and separating water using an appropriate drying agent, such as activated alumina, silica gel, molecular sieve, or activated carbon; and a low temperature separation method.

It is desirable that metallic sodium which is the catalyst for the reaction of alkylbenzene and 1,3-butadiene has a high purity, although it may contain a slight amount of calcium, magnesium, and potassium. The purity of 90% or higher, especially 99.0% or higher, is preferred.

The amount of metallic sodium used for the reaction is 0.001–2% by weight, preferably 0.005–1% by weight, and more preferably 0.05–1% by weight, of the total amount of the alkylbenzene and 1,3-butadiene to be reacted. If the amount of metallic sodium is less than 0.001% by weight, the catalytic activity is insufficient, while the amount greater than 2% by weight does not bring about any effects proportional to the excess amount.

In another embodiment of the present invention, a catalyst system comprising, in addition to the metallic sodium, an oxide, a hydroxide, or a salt of potassium, rubidium or an alkaline earth metal, or a mixture of these (hereinafter collectively referred to as "specific catalyst component") can be used for carrying out the above reaction. In this instance, the metallic sodium is preferably dispersed in the specific catalyst component.

Given as examples of the specific catalyst component are potassium oxide, potassium hydroxide, potassium carbonate, potassium sulfate, potassium chloride, potassium aluminate, rubidium oxide, rubidium hydroxide, rubidium carbonate, rubidium sulfate, calcium oxide, calcium hydroxide, calcium carbonate, calcium sulfate, calcium chloride, magnesium oxide, magnesium hydroxide, magnesium carbonate, magnesium sulfate, magnesium chloride, and the like. These specific catalyst components may be used either alone or in combination of two or more. Among these, preferred specific catalyst components are potassium hydroxide, potassium carbonate, potassium chloride, rubidium hydroxide, rubidium carbonate, calcium hydroxide, and calcium carbonate.

These specific catalyst components may contain sodium salts, such as sodium carbonate and sodium chloride, at a weight ratio of the specific catalyst components: sodium salts of about 10:1 to 1:10, preferably about 10:1 to 1:1. Inclusion of sodium salts in the specific catalyst component may occasionally promote the function of the catalyst used in the process of the present invention.

These specific catalyst components (hereinafter the "specific catalyst component" denotes those which may contain sodium salts) should be sufficiently dry. In particular, it is preferable that these specific catalyst components be sufficiently calcined at a high temperature of 200° C. to 600° C. in order to adequately promote their activity. Further, the specific catalyst components are preferably particles with a mean diameter of 100 μm or smaller, particularly 10 to 50 μm. Adjustment of the particle size can be carried out by sieve or the like.

Although there are no specific limitations to the ratio of metallic sodium and the specific catalyst component, the amount of metallic sodium is adjusted to have its final content in the catalyst of 0.1 to 30% by weight, preferably 0.5 to 20% by weight, and particularly preferably 1 to 10% by weight. If the amount of metallic sodium is smaller than 0.1 by weight, the action of the catalyst in the present invention is insufficient. The amount of metallic sodium greater than 30% by weight brings about no catalytic effects proportionate to the added amount, and only makes the process uneconomical.

A typical method of dispersing metallic sodium and the specific catalyst component comprises dispersing fine particles of metallic sodium and the specific catalyst component together. The dispersion-supporting is preferably carried out in an inert solvent. The master batch method or the method of preparing suspensions, each containing the metallic sodium or the specific catalyst component, and mixing the two suspensions are employed for homogeneously dispersing 0.1–30% by weight of metallic sodium and the specific catalyst component by dispersion-supporting in an inert solvent.

For example, in the case where 3% by weight of metallic sodium is dispersed in the specific catalyst component, 3 parts by weight of metallic sodium and 97 parts by weight of the specific catalyst component are together put into 1333 parts by weight of a solvent (alkylbenzene) and the mixture is stirred at a high speed at 110°–130° C. Alternatively, a suspension containing metallic sodium and the specific catalyst component at a suitable ratio is prepared in advance, and this suspension is further dispersed by the remaining specific catalyst component in the solvent (alkylbenzene).

Another method for the dispersion-supporting is mixing a suspension of 3 parts by weight of metallic sodium in 333 parts by weight of alkylbenzene and a suspension of 97 parts by weight of the specific catalyst component in 1000 parts by weight of alkylbenzene.

Still another method is preparing a suspension of 3 parts by weight of metallic sodium and 47 parts by weight of the specific catalyst component in 500 parts by weight of alkylbenzene and another suspension of 50 parts by weight of the specific catalyst component in 833 parts by weight of alkylbenzene, and then mixing the two suspensions.

In the industrial application of the inert solvent dispersion-supporting method, the same alkylbenzene as the raw material is preferably used as the solvent.

When the metallic sodium or a mixture of metallic sodium and the specific catalyst component is desired to be held fixed, such as the case where the reaction-distillation as hereinafter described is carried out, a molded catalyst made from a porous material with the metallic sodium or the mixture of metallic sodium and the specific catalyst component supported thereon can be used.

Besides the compounds mentioned above, faujasite X-zeolite and Y-zeolite, ion-exchanged mordenite, L-zeolite, potassium ion-exchanged resin, and the like can be used as the specific catalyst component. Because these are porous materials themselves, there are no need to use a separate porous material for supporting the catalytic component.

Given as examples of porous materials for holding the catalyst, are alumina, silica, silica alumina, X- and Y-zeolite, mordenite, pentasyl zeolite such as ZSM-5, L-zeolite, ion-exchanged resin, and naturally occurring clay minerals such as montmollilonite and sepiolite.

The following methods can be employed for supporting the metallic sodium or the mixture of metallic sodium and the specific catalyst component on a porous material.

One of the methods comprises molding the specific catalyst component, calcined in advance to a degree where there is no substantial amount of water contained therein, alone when the specific catalyst component is a porous material, or together with the porous material when the specific catalyst component is not a porous material, to produce molded particles with a particle size of 1.6 mm (⅛") or larger, followed by calcining the molded particles at 200°–500° C. In this instance, when molded particles in the shape of a ring, a saddle, or the like are desired, a molding binder, such as silica sol or alumina sol, can be used. As the molding method, tablet method, casting method, extrusion, or the like can be used with no specific limitations.

The particle size is not necessarily limited to 1.6 mm or larger. It is possible to use smaller size particles, e.g. as small as about 0.1 mm, by the same method of preparation mentioned above. However, in the case where the particle size is small, e.g. 0.1–1.6 mm, these particles are desirably filled in mesh containers, such as containers made from cloth, metallic wires, glasses fibers, polymer fibers, or the like, in order to avoid decrease in the fractionation distillation efficiency due to pressure loss caused by the small size particles. These types of containers are disclosed in U.S. Pat. No. 4,232,530, U.S. Pat. No. 4,242,530, U.S. Pat. No. 4,250,052, U.S. Pat. No. 4,302,356, and U.S. Pat. No. 4,307,251.

The following methods can be employed for carrying metallic sodium on the calcined dry material. One is a dry method which comprises saturating metallic sodium, melted at 65° to 700° C., preferably at 100° to 600° C., and more preferably at 200° to 500° C., in a dehydrated carrier gas inert to the metallic sodium, such as nitrogen, helium, or argon, and causing the melted metallic sodium to come into contact with the calcined dry material. The other is a wet method causing the melted metallic sodium as is or dispersed in an inert solvent to come into contact with the calcined dry material. Normal paraffins having 8–16 carbon atoms, alkylbenzenes, alkylnaphthalenes, or the like can be used as the solvent in the wet method. Of these, alkylbenzene, which is the raw material, is preferably used. The contact temperature in the wet method is preferably above the melting point of metallic sodium (97.8° C.) and below the boiling point of the solvent.

The catalyst with voids of 20 to 65 vol %, particularly 30 to 60 vol %, is preferably used in the process of the present invention.

The reaction of process of the present invention using the catalyst consisting of metallic sodium alone or a combination of the metallic sodium and the specific catalyst component is carried out under the pressure is 1 kPa (gauge) to 30 MPa (gauge), preferably 1 kPa (gauge) to 10 MPa (gauge), and more preferably 10 kPa (gauge) to 1 MPa (gauge).

If the pressure is smaller than 1 kPa (gauge), almost no target alkenyl compounds can be obtained by the reaction. If it is larger than 30 MPa (gauge), on the other hand, side-reaction products may be produced. The required pressure can be realized by the vapor pressure of the raw material compounds, for example, by heating alkylbenzene above its boiling point or by feeding 1,3-butadiene to the reaction system in a quantity greater than the quantity required for the reaction. Alternatively, feeding an inert gas can provide a desired pressure.

The molar ratio of alkylbenzene and 1,3-butadiene used in the reaction using the above-described catalyst and under the above-described pressure is suitably selected from the normal range; e.g., the approximate ratio of alkylbenzene:1,3-butadiene may be 1:0.001 to 1:0.5, preferably 1:0.01 to 1:0.4, and more preferably 1:0.05 to 1:0.3. The amount of alkylbenzene used as the solvent for the above-described dispersion treatment of metallic sodium and the specific catalyst component is accounted for this ratio of alkylbenzene and 1,3-butadiene.

It is desirable that the reaction of alkylbenzene and 1,3-butadiene in the process of the present invention be carried out substantially in the absence of water and oxygen. Water may convert metallic sodium into sodium hydroxide, resulting in decrease in its catalytic activity, and oxygen may deactivate the catalyst.

Therefore, the raw materials to be charged to the reaction system, i.e. alkylbenzene and 1,3-butadiene, are desirably those dehydrated.

Further, in order to avoid the presence of substantial amount of oxygen and water in the open spaces of the reaction system, it is desirable to fill the open spaces with dry inert gas, such as dry nitrogen or dry argon, or with the vapor of alkylbenzene or the like, when the reaction is carried out under pressurized reaction conditions above the boiling point of the alkylbenzene.

The reaction temperature in the process of the present invention is preferably about 50° C. to 200° C. If the temperature is lower than 50° C., by-products may be produced or it takes a longer period of time for the reaction. If it is higher than 200° C., production of the other by-products may increase. The reaction temperature from 80° C. to 180° C. is preferred.

The reaction time in the range of 0.05 to 10 hours is preferably applicable. The reaction time is dependent on the amount of the catalyst (g-catalyst), the composition of the catalyst (g-metallic sodium, g-specific catalyst component), the reaction temperature (°C.), the molar ratio of alkylbenzene and 1,3-butadiene (mol-alkylbenzene/mol-1,3-butadiene), the method of reaction (e.g. the batch reaction, the continuous reaction, etc. which will be hereinafter described), and the like. An appropriate reaction time is determined taking the purity of the target compounds, the manner in which the catalyst is used (e.g. adoption of catalyst recycle), and the like into consideration.

Generally, the reaction time is longer as the values for these factors decrease. The preferable reaction time is 0.1 to 8 hours, and particularly 0.3 to 5 hours.

Any reaction methods may be employed for the reaction in the process of the present invention. Such reaction methods include batch reaction in which the raw materials (alkylbenzene and 1,3-butadiene) and the catalyst, comprising metallic sodium or the combination of metallic sodium and the specific catalyst component, are charged altogether and reacted; semi-batch reaction in which alkylbenzene and the catalyst is first charged to the reactor and 1,3-butadiene is added as the reaction proceeds; continuous reaction in which alkylbenzene, 1,3-butadiene, and the catalyst are continuously charged to the reactor; and the reaction-distillation method in which alkylbenzene and 1,3-butadiene are introduced to the upper and lower parts, respectively, of a reactor column filled with the catalyst, and the target reaction products flow down to the bottom (illustrated hereinafter in more detail in reference to FIG. 1). Any suitable combinations of these methods can be also employed. Among these, the semi-batch reaction, the continuous reaction, or the reaction-distillation method are preferred, in order to suppress production of by-products such as 1,3-butadiene polymers or two or more mols of 1,3-butadiene addition compounds to alkylbenzene.

In the case of the continuous reaction, either of the following two methods can be employed due to the use of the solid catalyst. One is the method of feeding alkylbenzene continuously to the fixed catalyst bed, while introducing 1,3-butadiene to the alkylbenzene. The other method is effecting reaction while dispersing the catalyst with stirring in the reaction system consisting of alkylbenzene and 1,3-butadiene.

Any types of reactors, such as tubular-type, column-type, and vessel-type reactors, may be used for the continuous reaction.

One of the preferred manners of carrying out the continuous reaction is the crossing-flow type reaction method in which a plural number of reaction zones are provided and 1,3-butadiene is quantitatively fed to each reaction zone.

There are no specific limitations as to the reaction procedure inasmuch as alkylbenzene and 1,3-butadiene are sufficiently mixed and caused to come into contact with the catalyst, provided that in the case where 1,3-butadiene is introduced to the reaction system in which the catalyst is present, it is desirable to introduce alkylbenzene and 1,3-butadiene as a mixture, for example, as a liquid mixture consisting of liquid alkylbenzene and liquid 1,3-butadiene or as a vapor-liquid mixture consisting of gaseous 1,3-butadiene and liquid alkylbenzene. This is to prevent the inlet port from being choked up by rubber-like or resinous substance which are considered to be polymers of 1,3-butadiene. An alternative method of avoiding the choke-up is supplying 1,3-butadiene directly to the space where the reaction is taking place so as to ensure absorption and reaction of the 1,3-butadiene on the surface of reactants in which the catalyst is present.

Further, it is possible to introduce 1,3-butadiene by injection carried on a carrier gas. Injection can also provide the effect of agitation. An inert gas from which oxygen and water have been removed, such as nitrogen or argon, is preferably used here.

This reaction is preferably carried out under agitation. Introduction of gaseous 1,3-butadiene may provide the effect of agitation. The degree of agitation should be sufficient for homogeneously dispersing the catalyst throughout the reactor and for homogeneously mixing the raw materials and the products.

When the reaction is carried out in a liquid phase dispersion reaction system, the used catalyst may be separated by a known method, such as centrifugal precipitation, gravity precipitation, solid phase separation from a liquid-solid mixture at a low temperature (e.g. filtration, centrifuge), or the like.

The catalyst recovered can be recycled for reuse. Because the metallic sodium catalyst is converted into sodium hydroxide and loses the catalytic activity, fresh metallic sodium corresponding to the lost quantity is added to the catalyst before recycling for reuse.

In the case of the catalyst comprising metallic sodium and the specific catalyst component, the layer of the specific catalyst component is covered by the deactivated sodium hydroxide. Such a catalyst is oxidized and calcined to burn the organic substances attached thereto and to convert sodium hydroxide into sodium carbonate, following which the catalyst is regenerated for reuse by the addition of metallic sodium.

In the reaction-distillation method, the reaction time may be longer than the above-described reaction time, because it is difficult that two or more mols of 1,3-butadiene adduct to alkylbenzene, which is one type of the by-products, is produced by the reaction-distillation method. The reaction time in the reaction-distillation method can be determined chiefly from the feed rate of 1,3-butadiene and the catalyst fill length of the column.

The reaction-distillation method is now illustrated in detail referring to FIG. 1.

In FIG. 1, the catalyst is filled in the part 11 of the distillation column 10. The raw material alkylbenzene is supplied via line 1. This fresh alkylbenzene is combined with the unreacted alkylbenzene, which flows out from line 4 at the top of the column as effluent, is condensed in condenser 13, and sent via line 5 to vapor-liquid separator 14, where it is separated from unreacted 1,3-butadiene, which is drawn out from line 6. The alkylbenzene is then fed to column 10 from the top.

On the other hand, 1,3-butadiene is charged via line 2 to the lowest part of catalyst-fill section 11 of column 10 in gaseous or liquid state and caused to come into contact with alkylbenzene while it moves up to the top of the column, thereby producing an alkenyl compound.

Because the alkenyl compound produced has a boiling point higher than both alkylbenzene and 1,3-butadiene, it is liquid at temperatures at which alkylbenzene is present as both the vapor and the liquid. Thus, almost all alkenyl compound flows down to the bottom of the column.

This bottom product is drawn out from line 8 and sent to reboiler 12, where it is heated above the temperature at which the alkylbenzene is completely vaporized, but lower than the temperature at which all of the target alkenyl aromatic compound is vaporized, and sent back to reaction-distillation column 10 via line 9. The other portion of the column bottom product is cooled in cooler 15 and collected as the alkenyl compound product via line 3.

The pressure in the above reaction system is controlled in the range specified in the present invention, i.e. between 1 kPa (gauge) and 30 MPa (gauge), by the pressure-holding valve 16 which is provided in line 6.

Because the product from this reaction system once separated has no chance of coming into contact with 1,3-butadiene as in the case of the batch reaction system, the fluid collected via line 3 consists only of alkenyl aromatic compound which does not substantially contain unreacted alkylbenzene or by-produced di- or more substituents.

According to the process of the present invention, 5-phenylpentene is synthesized from toluene; 5-(o-tolyl)-pentene from o-xylene; 5-(p-tolyl)pentene from p-xylene; 5-(m-tolyl)pentene from m-xylene; and 5-(phenyl)hexene from ethylbenzene.

Japanese Patent Application No. 190080/1994 filed on Jul. 20, 1994 and No. 336045/1994 filed on Dec. 22, 1994 are herein incorporated as references.

Other features of the invention will become apparent in the course of the following description of the exemplary embodiments which are given for illustration of the invention and are not intended to be limiting thereof.

EXAMPLES

Example 1

0.45 part by weight of metallic sodium and 200 parts by weight of o-xylene were charged to a 500 ml pressure autoclave equipped with a stirrer having half-moon-shaped blades. After stirring at 500 rpm at 140° C. for one hour, the temperature was raised to 150° C. and argon gas was introduced to bring the pressure to 100 kPa (gauge). 1,3-butadiene was then introduced at a flow rate of 27.0 ml/min for 3 hours.

The reaction mixture was cooled to 100° C. immediately after the reaction to separate the metallic sodium from the reaction solution. After washing with distilled water until the mixture is neutralized, the excess amount of o-xylene was evaporated, and the residue was distilled under reduced pressure to obtain 5-(o-tolyl)-pentene. The yield and purity of the 5-(o-tolyl)pentene was measured. The results are shown in Table 1. Examples 2–15, Comparative Examples 1–2

5-(o-tolyl)pentene was prepared in the same manner as in Example 1, provided that the composition of the catalyst, reaction pressure and temperature listed in Table 1 were employed, and further that the stirring was carried out at rotation of 1200 rpm for Comparative Examples 1–2.

The yield and purity of the 5-(o-tolyl)pentene were measured. The results are shown in Table 1.

TABLE 1

|   | Reaction pressure kPa (gauge) | Reaction temperature (°C.) | Reaction time (hour) | Catalyst Metallic Na (wt %)* | Product Yield (%) | Product Purity (%) |
|---|---|---|---|---|---|---|
| Example |  |  |  |  |  |  |
| 1 | 100 | 150 | 3 | 0.23 | 85 | 99 |
| 2 | 100 | 150 | 1.5 | 0.23 | 91 | 99 |
| 3 | 100 | 150 | 6 | 0.23 | 78 | 99 |
| 4 | 100 | 150 | 14 | 0.23 | 65 | 98 |
| 5 | 100 | 140 | 3 | 0.23 | 85 | 99 |
| 6 | 200 | 140 | 3 | 0.23 | 85 | 99 |
| 7 | 200 | 140 | 3 | 0.10 | 85 | 99 |
| 8 | 200 | 140 | 3 | 0.08 | 84 | 99 |
| 9 | 200 | 160 | 3 | 0.23 | 84 | 98 |
| 10 | 400 | 120 | 3 | 0.20 | 86 | 99 |
| 11 | 1000 | 120 | 3 | 0.20 | 82 | 98 |
| 12 | 20000 | 105 | 3 | 0.10 | 63 | 96 |
| 13 | 10 | 140 | 3 | 0.23 | 57 | 98 |
| 14 | 100 | 140 | 3 | 2.00 | 85 | 99 |
| 15 | 100 | 150 | 3 | 0.005 | 78 | 98 |
| Comparative Example |  |  |  |  |  |  |
| 1 | 0 | 140 | 3 | 0.23 | 0 | — |
| 2 | 0 | 145 | 3 | 0.23 | 0 | — |

*Na wt % is based for the amount of alkylbenzene.

It is clear from Table 1 that the target 5-(o-tolyl)pentene can be prepared at a high yield by the process of the present invention. Examples 16–25, Comparative Examples 3–4

5-(p-tolyl)pentene was prepared in the same manner as in Example 1, except that p-xylene was used instead of o-xylene and the catalysts with the composition shown in Table 2 were used.

The yield and purity of the 5-(p-tolyl)pentene were measured. The results are shown in Table 2.

TABLE 2

|   | Reaction pressure kPa (gauge) | Reaction temperature (°C.) | Reaction time (hour) | Catalyst Metallic Na (wt %)* | Product Yield (%) | Product Purity (%) |
|---|---|---|---|---|---|---|
| Example |  |  |  |  |  |  |
| 16 | 100 | 150 | 3 | 0.23 | 86 | 99 |
| 17 | 100 | 150 | 1.5 | 0.23 | 92 | 99 |
| 18 | 100 | 150 | 7 | 0.23 | 75 | 98 |
| 19 | 200 | 140 | 3 | 0.20 | 85 | 99 |
| 20 | 100 | 150 | 3 | 0.10 | 85 | 99 |
| 21 | 100 | 120 | 3 | 0.23 | 83 | 98 |
| 22 | 10 | 150 | 3 | 0.20 | 49 | 99 |
| 23 | 100 | 140 | 3 | 0.005 | 80 | 98 |
| 24 | 20000 | 105 | 3 | 0.10 | 57 | 98 |
| 25 | 100 | 150 | 3 | 2.00 | 85 | 99 |
| Comparative Example |  |  |  |  |  |  |
| 3 | 0 | 140 | 3 | 0.23 | 0 | — |
| 4 | 0 | 145 | 3 | 0.23 | 0 | — |

*Na wt % is based for the amount of alkylbenzene.

It is clear from Table 2 that the target 5-(p-tolyl)pentene can be prepared at a high yield by the process of the present invention.

Examples 26–27

5-(m-tolyl)pentene or 5-(phenyl)hexane was prepared in the same manner as in Example 1, except that m-xylene (Example 26) or ethylbenzene (Example 27) was used instead of o-xylene.

The yield and purity of the 5-(m-tolyl)pentene or 5-(phenyl)hexane were measured. The results are shown in Table 3.

TABLE 3

|  | Raw material | Product | |
|---|---|---|---|
|  |  | Yield (%) | Purity (%) |
| Example 26 | m-Xylene | 83 | 98 |
| Example 26 | Ethylbenzene | 85 | 99 |

Example 28

0.45 part by weight of metallic sodium, 15.0 parts by weight of potassium carbonate, and 200 parts by weight of o-xylene were charged to a 500 ml pressure autoclave equipped with a stirrer having half-moon-shaped blades. After stirring at 500 rpm at 140° C. for one hour, the temperature was raised to 150° C. and argon gas was introduced to bring the pressure to 100 kPa (gauge). 1,3-butadiene was then introduced at a flow rate of 27.0 ml/min for 3 hours.

The reaction mixture was cooled to 100° C. immediately after the reaction to separate the catalyst from the reaction solution. After washing with distilled water until the mixture was neutralized, the excess amount of o-xylene was evaporated, and the residue was distilled under reduced pressure to obtain 5-(o-tolyl)-pentene. The yield and purity of the 5-(o-tolyl)pentene was measured. The results are shown in Table 4.

Examples 29–32, Comparative Example 5

5-(o-tolyl)pentene was prepared in the same manner as in Example 28, provided that the composition of the catalyst, reaction pressure and temperature listed in Table 4 were employed, and further that the stirring was carried out at a rotation of 1200 rpm for Comparative Example 5.

The yield and purity of the 5-(o-tolyl)pentene were measured. The results are shown in Table 4.

TABLE 4

|  | Reaction pressure kPa (gauge) | Reaction temp. (°C.) | Catalyst* | | Product | |
|---|---|---|---|---|---|---|
|  |  |  | Metallic sodium | Specific cat. component | Yield (%) | Purity (%) |
| Example |  |  |  |  |  |  |
| 28 | 100 | 150 | 0.23 | ($K_2CO_3$) 7.5 | 72.0 | 99 |
| 29 | 40 | 140 | 0.23 | ($K_2CO_3$) 7.5 | 49.0 | 99 |
| 30 | 100 | 150 | 0.23 | ($K_2CO_3$) 2.5  ($Rb_2CO_3$) 5.0 | 69.0 | 98 |
| 31 | 50 | 145 | 0.23 | ($K_2CO_3$) 5.0  (KOH) 2.5 | 70.0 | 99 |
| 32 | 1000 | 140 | 0.23 | ($K_2CO_3$) 7.5 | 78.0 | 97 |
| Comparative Example |  |  |  |  |  |  |
| 5 | 0 | 145 | 0.23 | ($K_2CO_3$) 7.5 | 2.0 or less | — |

*The amounts indicates wt % for the amount of alkylbenzene.

It is clear from Table 4 that the target 5-(p-tolyl)pentene can be prepared at a high yield by the process of the present invention.

Examples 33–35, Comparative Example 6

5-(p-tolyl)pentene was prepared in the same manner as in Example 28, except that p-xylene was used instead of o-xylene and the catalysts with the composition shown in Table 5 were used.

The yield and purity of the 5-(p-tolyl)pentene were measured. The results are shown in Table 5.

TABLE 5

| | Reaction pressure kPa (gauge) | Reaction temp. (°C.) | Catalyst* Metallic sodium | Catalyst* Specific cat. component | | Product Yield (%) | Product Purity (%) |
|---|---|---|---|---|---|---|---|
| Example | | | | | | | |
| 33 | 150 | 150 | 0.23 | (K$_2$CO$_3$) 7.5 | | 71.5 | 99 |
| 34 | 100 | 150 | 0.23 | (K$_2$CO$_3$) 5.0 | (KOH) 2.5 | 69.5 | 98 |
| 35 | 50 | 145 | 0.23 | (K$_2$CO$_3$) 7.5 | | 70.0 | 99 |
| Comparative Example | | | | | | | |
| 6 | 0 | 145 | 0.23 | (K$_2$CO$_3$) 7.5 | | 2.0 or less | — |

*The amount indicates wt % for the amount of alkylbenzene.

It is clear from Table 5 that the target 5-(p-tolyl)pentene can be prepared at a high yield by the process of the present invention.

Example 36

(1) Preparation of a dispersion solution of metallic sodium 2 parts by weight of metallic sodium was charged to 100 parts of by weight of o-xylene, of which the water content was reduced to below 0.1 ppm with zeolite in advance. The metallic sodium was finely pulverized by a mechanical stirrer at 120° C. under high purity nitrogen atmosphere.

(2) Preparation of a potassium-type Y-zeolite carrier

A commercially available proton-type Y-zeolite was suspended in water. An aqueous solution of potassium hydroxide (1N) was added dropwise to the suspension to make the pH 12, following which the suspension was filtered and sufficiently washed, thus obtaining a potassium-type Y-zeolite.

Dry boehmite alumina in an amount of 20 parts by weight, as aluminum oxide, was added to 80 parts by weight of the potassium-type Y-zeolite which was dried at 130° C. The mixture was thoroughly blended, deflocculated with the addition of 1N aqueous solution of nitric acid, and neutralized with ammonia water. The clay-like material thus obtained was molded into rings. The molded products were dried at 130° C. and calcined at 550° C. to obtain rings with an outer size of 3 mmφ×3 mm.

(3) Preparation of a metallic sodium-potassium type Y-zeolite carrier composite 10 parts by weight of the sodium-potassium type Y-zeolite carrier prepared in (2) above, was added to 100 parts by weight of o-xylene with a water content of below 0.1 ppm. To the mixture was added 100 parts by weight of the dispersion of metallic sodium prepared in (1) above, and the resulting mixture was stirred at a high speed with a mechanical stirrer, followed by evaporation of o-xylene.

(4) Synthesis of 5-(o-tolyl)pentene

The metallic sodium-potassium type Y-zeolite carrier composite prepared in (3) was transferred to a packing column (30 mmφ×500 mm) of a distillation device equipped with this column and a 1000 ml three-necked flask, to fill out the upper 60% area of the column (an amount as catalyst: 200 ml). A coil filler (Helipack, trademark, manufactured by Nitto Han-noki Co.) was filled in the remaining part of the column.

300 ml of o-xylene with a water content of below 0.1 ppm was charged to the three-necked flask and heated to the boiling point, thereby evaporating o-xylene vapor up to the column top. The pressure was raised to 50 kPa (gauge) and the system was stabilized, while refluxing the whole amount.

Then, 1.3-butadiene was supplied from one of the ports of the three-necked flask at a rate of 10 ml/min.

After reacting for 3 hours in this manner, o-xylene was evaporated under reduced pressure to obtain 5-(o-tolyl) pentene. The yield and purity of 5-(o-tolyl)pentene were analyzed. The results shown in Table 6.

Example 37

The same experiment as in Example 36 was carried out, except that in the preparation of the sodium-potassium type Y-zeolite carrier prepared in Example 36 (2) a potassium carbonate powder was used instead of the potassium-type Y-zeolite and aluminum hydroxide gel was used instead of the dry boehmite alumina. The results are shown in Table 6.

Examples 38–39

The same experiment as in Example 36 was carried out, except that m-xylene (Example 38) or p-xylene (Example 39) was used instead of o-xylene.

The results are shown in Table 6.

TABLE 6

| | Raw material | Product Yield (%) | Product Purity (%) |
|---|---|---|---|
| Example 36 | o-Xylene | 75.0 | 98 |
| Example 37 | o-Xylene | 73.5 | 98 |
| Example 38 | m-Xylene | 72.5 | 98 |
| Example 39 | p-Xylene | 69.0 | 98 |

Example 40

The same apparatus as used in Example 36(4) was used, except for using a 300 ml flask in the bottom. 50 ml of 5-(o-tolyl)pentene, prepared in advance, was charged and heated to the boiling point to vaporize 5-(o-tolyl)pentene up to the top of the column and to reflux the whole amount.

Then, o-xylene was fed from the bottom of the distillation column at a flow rate of 100 ml (liquid)/hour, while heating the flask to 150° C. (a temperature above the boiling point of o-xylene) so as to prevent the o-xylene from coming down to the flask. The pressure was raised to 50 kPa (gauge). After the system was stabilized, 1.3-butadiene was fed from one of the ports of the three-necked flask at a rate of 600 ml (gas )/hour.

Feeding the raw materials was terminated after a two hour reaction. Then, after evaporating o-xylene in the distillation column, the flask was cooled and its content was weighed, to find that the weight of the product was 58.5 g (60 ml). The purity of the 5-(o-tolyl)pentene was 99%.

Based on the results, the amount of 5-(o-tolyl)pentene produced (excluding the initially charged 5-(o-tolyl) pentene) in the reaction for two hours was found to be 8.5 g, confirming that almost 100% of the 1,3-butadiene charged was converted into the target product.

The process of the present invention exhibits the following effects.

(1) It is possible to manufacture alkenyl compounds very efficiently at a greatly increased yield.

(2) It is possible to carry out a highly active and selective alkenylation reaction at a low cost by employing a specified reaction pressure and using the catalyst which is easy to handle.

(3) The production of unwanted side reaction products which are difficult to separate from the target compound can be suppressed. Thus, a high purity target product can be obtained at a high yield.

(4) The catalyst components used are inexpensive, safe, free from any danger, and readily separable from the reaction mixture. There are no need for the use of components such as metallic sodium-potassium alloy which is expensive, has a risk of being ignited, and is difficult to separate from the reaction mixture.

Obviously, numerous modifications and variations of the present invention are possible in light of the above teachings. It is therefore to be understood that within the scope of the appended claims, the invention may be practiced otherwise than as specifically described herein.

I claim:

1. A process for manufacturing an alkenyl compound which comprises reacting an alkylbenzene and 1,3-butadiene in the presence of metallic sodium as sole catalyst under a pressure of 10 kPa (gauge) to 1 MPa (gauge).

2. The process according to claim 1, wherein the amount of metallic sodium used for the reaction is 0.001–2% by weight of the total amount of alkylbenzene and 1,3-butadiene.

3. The process according to claim 1, wherein the alkylbenzene is toluene, ethylbenzene, o-xylene, m-xylene, p-xylene, trimethylbenzene, tetramethylbenzene, or pentamethylbenzene.

4. The process according to claim 1, wherein the ratio of alkylbenzene:1,3-butadiene is 1:0.001 to 1:0.5.

5. The process according to claim 1, wherein the reaction is carried out substantially in the absence of water and oxygen.

6. The process according to claim 1, wherein the metallic sodium is molded together with a porous material.

7. The process according to claim 6, wherein the porous material is selected from the group consisting of alumina, silica, silica alumina, X-zeolite, Y-zeolite, mordenite, pentasyl zeolite, L-zeolite, ion-exchanged resin, montmollilonite, and sepiolite.

* * * * *